United States Patent [19]
Griffiths et al.

[11] Patent Number: 5,846,741
[45] Date of Patent: Dec. 8, 1998

[54] BORON NEUTRON CAPTURE THERAPY USING PRE-TARGETING METHODS

[75] Inventors: Gary L. Griffiths, Morristown; Serengulam V. Govindan, Summit, both of N.J.

[73] Assignee: Immunomedics, Inc., Morris Plains, N.J.

[21] Appl. No.: 687,626

[22] Filed: Jul. 26, 1996

Related U.S. Application Data

[63] Continuation-in-part of Ser. No. 486,166, Jun. 7, 1995, abandoned, and Ser. No. 456,393, Jun. 1, 1995, Pat. No. 5,698,405, which is a division of Ser. No. 933,982, Aug. 21, 1992, Pat. No. 5,525,338.

[51] Int. Cl.$^6$ .................................................. G01N 33/53
[52] U.S. Cl. ...................... 435/7.5; 424/1.37; 424/1.53; 424/155.1; 435/7.23; 530/388.8; 530/388.85
[58] Field of Search ................................. 424/1.37, 1.53, 424/155.1; 435/7.23, 7.5; 530/388.85, 388.8

[56] References Cited

U.S. PATENT DOCUMENTS

| | | | |
|---|---|---|---|
| 4,179,337 | 12/1979 | Davis et al. ............................ | 435/181 |
| 4,624,846 | 11/1986 | Goldenberg . | |
| 4,732,863 | 3/1988 | Tomasi et al. ........................... | 436/547 |
| 4,863,713 | 9/1989 | Goodwin et al. . | |
| 5,443,813 | 8/1995 | Hainfeld . | |
| 5,462,724 | 10/1995 | Schinazi et al. . | |
| 5,482,698 | 1/1996 | Griffiths . | |
| 5,525,338 | 6/1996 | Goldenberg . | |
| 5,612,017 | 3/1997 | Miura et al. . | |

FOREIGN PATENT DOCUMENTS

| | | |
|---|---|---|
| 0 251494 | 5/1987 | European Pat. Off. . |
| 89/10140 | 11/1989 | WIPO . |
| 96/14073 | 5/1996 | WIPO . |

OTHER PUBLICATIONS

Mehta et al., "Targeted Drug Delivery for Boron Neutron Capture Therapy", Parmaceutical Research, vol. 13, No. 3, pp. 344–351 (1996).

Sinitsyn, et al. "Use of Avidin for Enhanced Blood Clearance of Biotinylated Immunoglobulins," Byull. Eksp. Biol. Med., 109:6 pp. 567–569 Russian with English/ abstract (1990).

Paganelli, et al. "Tumor Targeting in Patients with Ovarian Cancer Using Biotinylated Monoclonal Antibodies and Radioactive Streptavidin," J. Nucl. Med., 31:5 p. 735 (May 1990), Abstract No. 117.

Hnatowich, et al. "Investigations of Avidin and Biotin for Imaging Applications," J. Nucl. Med., 28:8 pp. 1294–1302 (1987).

Paganelli, et al. "Three–Step Monoclonal Antibody Tumor Targeting in Carcinoembryonic Antigen–positive Patients," Cancer Res., 51:21 pp. 5960–5966 (Nov. 1991).

Kalofonos, et al. "Imaging of Tumor Patients with Indium–111–Labeled Biotin and Streptavidin–Conjugated Antibodies: Preliminary Communications," J. Nucl. Med., 31:11 pp. 1791–1796 (Nov. 1990).

Fuccillo, D.A. "Application of the Avidin–Biotin Technique in Microbiology," Bio Techniques 3:5 pp. 494–501 (1985).

Ferro et al. "Antibody Targeting of Boron Compounds" :Proceedings of the Fourth International Symposium on Neutron Capture Therapy for Cancer Held Dec. 4–7, 1990 in Progress in Neutron Capture Therapy/for Cancer, Plenum Press, New York, pp. 269–271, 1992.

Holmberg et al., "Preparation of Sulfhydrylborane–Dextran Conjugates for Boron Neutron Capture Therapy," Bioconjugate Chemistry, 4 (1993) 570–3.

Komura et al., "Thermal Neutron Capture Therapy of Malignant Melanoma Using $^{10}$B–Monoclonal Antibodies: in vitro and in vivo Analysis," Melanoma Research, 1 (1991): 397–403.

Primary Examiner—Carol A. Spiegel
Attorney, Agent, or Firm—Foley & Lardner

[57] ABSTRACT

The present invention provides a method for targeting boron atoms to tumor cells in a patient. The method comprises the steps of:

(A) administering a targeting composition comprising a conjugate of a first member of a binding pair and an antibody, wherein the antibody selectively binds to antigens produced by or associated with the tumor cells, and allowing the conjugate to localize at said tumor cells;

(B) optionally, administering a clearing composition, and allowing the clearing composition to clear non-localized conjugate from circulation;

(C) administering a boron-containing compound comprising a conjugate comprising a complementary member of said binding pair and boron atoms, and allowing the compound to localize at the tumor cells. The method may further comprise the step of irradiating the boron atoms of the boron compound, thereby effecting BNCT of the tumor cells. Compositions and kits for carrying out the method also are provided.

34 Claims, No Drawings

BORON NEUTRON CAPTURE THERAPY USING PRE-TARGETING METHODS

This application is a continuation-in-part of U.S. application Ser. No. 08/486,166, filed Jun. 7, 1995, now abandoned. This application is also a continuation-in-part of U.S. application Ser. No. 08/456,393, filed Jun. 1, 1995, now U.S. Pat. No. 5,698,405, which is a divisional of U.S. application Ser. No. 07/933,982, filed Aug. 21, 1992, now U.S. Pat. No. 5,525,338.

BACKGROUND OF THE INVENTION

1. Field of the Invention

The present invention relates to improved methods for targeting boron atoms to tumor cells for effecting boron neutron capture therapy (BNCT). BNCT is a binary system designed to deliver ionizing radiation to tumor cells by neutron irradiation of tumor-localized boron-10 atoms. In the present invention, the cancer cells are pre-targeted, for example, with a carcinoembryonic antigen-specific monoclonal antibody (MAb) conjugated to, for example, streptavidin. Then, a boron-containing compound conjugated to, for example biotin, is administered which binds to the streptavidin localized at the cancer site. The localized boron may then be irradiated, thereby effecting treatment of the tumor cells.

2. Description of Related Art
BORON NEUTRON CAPTURE THERAPY

Boron neutron capture therapy (BNCT) is based on the nuclear reaction which occurs when a stable isotope, B-10 (present in 19.8% natural abundance), is irradiated with thermal neutrons to produce an alpha particle and a Li-7 nucleus. These particles have a path length of about one cell diameter, resulting in high linear energy transfer. Just a few of the short-range 1.7 MeV alpha particles produced in this nuclear reaction are sufficient to target the cell nucleus and destroy it. Barth et al., *Cancer*, 70: 2995–3007 (1992). Since the $^{10}B(n,\alpha)^7Li$ reaction will occur, and thereby produce significant biological effect, only when there is a sufficient fluence (number) of thermal neutrons and a critical amount of B-10 localized around or within the malignant cell, the radiation produced is localized. The neutron capture cross section of B-10 far exceeds that of nitrogen and hydrogen found in tissues, which also can undergo capture reactions, (relative numbers: 1 for N-14, 5.3 for H-1, and 11560 for B-10), so that once a high concentration differential of B-10 is achieved between normal and malignant cells, only the latter will be affected upon neutron irradiation. This is the scientific basis for boron neutron capture therapy. Barth et al., supra; Barth et al. *Cancer Res.*, 50: 1061–70 (1990); Perks et al., *Brit. J. Radiol.*, 61: 1115–26 (1988).

Nuclear reactors are the source of neutrons for BNCT. Thermal neutron beams with energies in the range of 0.023 eV, used in early experiments for treating brain tumors, are easily attenuated by tissues, and are poorly penetrating. More recent advances with neutrons of intermediate energy (epithermal neutrons, 1–10,000 eV energy) have led to the consensus for its use in planned clinical trials in the U.S. and Europe. Alam et al., *J. Med. Chem.*, 32: 2326–30 (1989). Fast neutrons with a probable energy of 0.75 MeV are of little use in BNCT.

Original calculations estimated that a boron concentration of 35–50 $\mu$g per gram of tumor, or $10^9$ B-10 atoms per tumor cell, would be necessary to sustain a cell-killing nuclear reaction with thermal neutron fluences of $10^{12}$–$10^{13}$ n.cm$^{-2}$. Fairchild et al., *Int. J. Radiat. Oncol. Biol. Phys.*, 11: 831 (1985). These calculations were based on uniformly distributed boron, as seen with non-specific boronated compounds. For antibody-based boron agents, assuming saturation of all surface antigens on the tumor cell, this level of boron requirement translates to about 1000 atoms per antibody molecule. However, more recent Monte Carlo calculations led to the analysis that for a non-internalizing antibody, boron loading could be as low as 300 atoms per MAb molecule. Kalend et al., *Med. Phys.*, 18: 662 (1991); Zamenhof et al., *J. Nat'l Cancer Inst.*, 84: 1290–91 (1992).

This was based on the following rationale: for tumor cells exhibiting a nucleus-to-cell volume ratio of 0.5 and an effective cell diameter of 10 $\mu$m, three B-10 fissions on the cell surface would produce at least one heavy particle trajectory into the nucleus. Assuming saturation of antigen sites on the cell surface, it was deduced that under these conditions just 300 atoms per antibody molecule would suffice to bring about the three fission reactions on the tumor cell surface. The present invention describes a method which can attach a 20-fold greater number of boron atoms per MAb than these prior methods entailed.

Historically, BNCT was first employed for the treatment of glioblastoma (a fatal form of brain tumor) and other brain tumors at a time when tumor specific substances were almost unknown. Hatanaka et al., in BORON NEUTRON CAPTURE THERAPY FOR TUMORS, pp. 349–78 (Nishimura Co., 1986). One of the first boronated compounds employed, a sulfhydryl-containing boron substance called sodium borocaptate or BSH ($Na_2, B_{12}H_{11}SH$), crosses the blood-brain barrier to localize in brain, and this has been the anatomical basis for neutron capture therapy of brain tumors. Clinical trials have been carried out, or are scheduled, for the treatment of gliomas in Japan, the US and Europe. Barth et al., *Cancer*, supra. Problems with previous inorganic boron therapy methods was that the boron reached both targeted and non-target areas. Accordingly, when the boron was irradiated, healthy cells as well as cancerous cells were destroyed.

The BNCT concept has been extended to other cancers, spurred on by the discovery of a number of tumor-localizing substances, including tumor-targeting monoclonal antibodies. For instance, boronated amino acids such as p-boronophenylalanine accumulated in melanoma cells. The potential of using boronated monoclonal antibodies directed against cell surface antigens, such as CEA, for BNCT of cancers has been demonstrated. Ichihashi et al., *J. Invest. Dermatol.*, 78: 215–18 (1982); Goldenberg et al., *P.N.A.S., USA*, 81:560–63 (1984); Mizusawa et al. *P.N.A.S., USA*, 79: 3011–14 (1982); Barth et al., *Hybridoma*, 5(supp. 1): 543–5540 (1986); Ranadive et al. *Nucl. Med. Biol.*, 20: 663–68 (1993). However, heavily boronated antibodies failed to target tumor in vivo in animal models. Alam et al., supra; Barth et al., *Bioconjugate Chem.*, 5: 58–66 (1994).

Success with BNCT of cancer requires methods for localizing a high concentration of boron-10 at tumor sites, while leaving non-target organs essentially boron-free. Non-antibody boronated compounds which accumulate in tumor preferentially, but not specifically, have the disadvantage that tumor-to-blood and tumor-to-organ ratios are often less than ideal, with the result that damage to normal organs could occur during irradiation with neutron beams.

In the case of antibodies, the perceived need to load the same with 1000 boron atoms per antibody molecule has led to the design of a variety of heavily boronated antibodies using, for instance, polylysine, dendrimer or dextran as intermediate carriers of boron clusters. Alam et al., supra; Barth et al., *Bioconjugate Chem.*, supra. Although in many instances some antigen-binding was found to be retained in vitro, these boronated conjugates predominantly localized in liver with little accretion in tumor in in vivo animal tumor models.

Thus, there is need for a method of targeting boron atoms to tumor cells that is able to deliver a large amount of boron atoms to tumor sites, while leaving non-cancerous sites relatively boron-free.

PRE-TARGETING

The concept of pre-targeting for in vivo imaging application was proposed by Hnatowich et al., *J. Nucl. Med.*, 28: 1294–1302 (1987), and was later examined from a theoretical viewpoint. Van Osdol et al., *J. Nucl. Med.*, 34: 1552–64 (1993). Pre-targeting has been recently reported to have resulted in very encouraging preclinical results with yttrium-90 radioimmunotherapy. Axworthy et al., *J. Immunother.*, 16: 158 (1994). U.S. application Ser. No. 07/933,982 (filed Aug. 21, 1992, issue fee paid Dec. 28, 1995), U.S. Pat. No. 5,482,698, U.S. application Ser. No. 08/409,960 (filed Mar. 25, 1995, pending), and U.S. application Ser. No. 08/486,166 (filed Jun. 7, 1995, pending) also disclose various pre-targeting methods. The contents of all of these references are incorporated herein in their entirety by reference.

Therapy requires a high absolute accretion of the therapeutic agent at the cancer site, as well as a reasonably long duration of uptake and binding. High background levels of non-targeting antibody have long been recognized as a major impediment to high target: background ratios being achieved. To overcome this impediment, various methods have been developed, such as those described in Hansen et al., U.S. Pat. No. 3,927,193 and Goldenberg, U.S. Pat. Nos. 4,331,647, 4,348,376, 4,361,544, 4,468,457, 4,444,744, 4,460,459, 4,460,561, 4,624,846 and 4,818,709, the disclosures of all of which are incorporated herein by reference.

Pre-targeting methods using biotin/avidin approaches are described, for example, in Hnatowich et al., *J. Nucl. Med.* 28: 1294, 1987; Oehr et al., *J. Nucl. Med.* 29: 728, 1988; Klibanov et al., *J. Nucl. Med.* 29: 1951, 1988; Sinitsyn et al., *J. Nucl. Med.* 30: 66, 1989; Kalofonos et al., *J. Nucl. Med.* 31: 1791, 1990; Schechter et al., *Int. J. Cancer* 48: 167, 1991; Paganelli et al., *Cancer Res.* 51: 5960, 1991; Paganelli et al., *Nucl. Med. Commun.* 12: 211, 1991; Stickney et al., *Cancer Res.* 51: 6650, 1991; and Yuan et al., *Cancer Res.* 51: 3119, 1991; all incorporated herein in their entirety by reference.

These methods involve pre-targeting a target site, such as a tumor or lesion, with a targeting protein, such as an antibody or antibody fragment, conjugated to one member of a binding pair, such as biotin or avidin, whereby the antibody conjugate localizes at the target site. Then, a conjugate of a detection or therapeutic agent, such as a radioisotope, and the complementary member of the binding pair, such as avidin or biotin, is administered. The binding affinity between the members of the binding pair causes the second conjugate to localize at the target site, where the first conjugate already is bound.

In some of these methods, an intermediate clearing or localizing step is used. In this case, the first conjugate comprises one member of the binding pair (for example, biotin), the clearing and localizing agent may comprise the other member of the binding pair (for example, avidin), and the second conjugate comprises the same member of the binding pair as the first (for example, biotin). Other clearing agents, such as antibodies, also have been described.

There is a need for a method of targeting boron atoms to tumor cells that obtains high tumor:non-tumor ratios of the boron atoms, and that delivers sufficient amounts of boron atoms to tumor sites in an efficient manner. Compositions suitable for use in such a method also are needed.

SUMMARY OF THE INVENTION

It is therefore an object of the present invention to provide a method for targeting boron atoms to tumor cells that overcomes the previous problems of maintaining a high tumor:non-tumor ratio of boron-10 atoms, and for delivering sufficient amounts of boron-10 atoms to tumor sites efficiently, and to provide compositions for use in this method.

In accomplishing these and other objects of the invention, there is provided, in accordance with one aspect of the present invention, a method for targeting boron atoms to tumor cells in a patient, comprising the steps of:

(A) administering to the patient a targeting composition comprising a conjugate of a first member of a binding pair and an antibody, wherein the antibody selectively binds to antigens produced by or associated with the tumor cells, and allowing the conjugate to localize at the tumor cells;

(B) optionally, administering to the patient a clearing composition, and allowing the clearing composition to clear non-localized conjugate from circulation; and (C) administering to the patient a boron-containing compound comprising a conjugate comprising a complementary member of the binding pair and boron atoms, and allowing said boron-containing compound to localize at the tumor cells. The method may further comprise the step of irradiating the boron atoms of the boron-containing compound localized at the tumor cells, thereby effecting BNCT of the tumor cells.

The binding pair may comprise biotin and avidin or streptavidin, complementary strands of polynucleotides, or enzyme-substrate pairs. When the binding pair comprises biotin, the biotin may comprise a biotinidase-resistant biotin analog comprising a biotin moiety peptide-bonded to an unnatural D-amino acid.

In one embodiment of the present invention, the boron-containing compound is radiolabeled with a detectable label, in which case the method may further comprise the step of detecting the detectable label of the boron-containing compound, thereby determining the location of the compound. In another embodiment of the present invention, the boron atoms of the boron-containing compound localized at the tumor cells are irradiated after the detectable label is detected.

In accordance with another aspect of the present invention there is provided a sterile, injectable composition for human use comprising a composition for use in targeting boron atoms to tumor cells, comprising a biotin-containing compound comprising a conjugate of a member of a binding pair and boron atoms. In one embodiment of the invention, the biotin-containing compound is radiolabeled with a detectable label.

The member of the binding pair may comprise biotin or avidin or streptavidin, a single strand of a polynucleotide, or an enzyme or enzyme substrate. When the member of the binding pair comprises biotin, the biotin may comprise a biotinidase-resistant biotin analog comprising a biotin moiety peptide-bonded to an unnatural D-amino acid.

In accordance with another aspect of the present invention, there is provided a kit suitable for use in a method for targeting boron atoms to tumor cells in a patient, the kit comprising:

(A) a sterile, injectable preparation of a targeting composition comprising a first member of a binding pair and an antibody, wherein the antibody selectively binds to antigens produced by or associated with the tumor cells;

(B) optionally, a clearing composition; and (C) a boron-containing compound comprising a conjugate comprising a complementary member of the binding pair and boron atoms.

Additional objects and advantages of the invention are set forth in part in the description that follows, and in part will be obvious from the description, or may be learned by practice of the invention. The objects and advantages may be realized and obtained by means of the processes and compositions particularly pointed out in the appended claims.

DETAILED DESCRIPTION OF THE PREFERRED EMBODIMENTS

The present invention overcomes the aforementioned problems with antibody-targeted BNCT by decoupling the antibody and boron delivery steps by using, for example, a two- or three-step pre-targeting procedure. While prior methods of antibody-targeted BNCT involve loading about 1500 boron-10 atoms onto a single molecule of antibody, the present invention does not load the targeting antibody with boron, thereby eliminating the problems associated with boron-mAb hyper-substitution.

In the present invention, a high concentration of boron is specifically localized at the tumor sites by pre-targeting the tumor sites with a tumor antigen selective monoclonal antibody conjugated to one member of a binding pair, such as avidin or streptavidin. The antibody used selectively binds to antigens produced by or associated with tumor cells. The use of a selective monoclonal antibody is inherently more specific than the previously used boronated compounds which accumulate in tumor sites preferentially, but not selectively.

After the antibody-avidin conjugate has localized at the tumor sites, and, optionally, after a clearing agent has been administered and allowed to clear non-localized conjugate from circulation, a boron-containing compound comprising a conjugate comprising the complementary member of the binding pair, such as biotin, and boron is administered. The affinity between the members of the binding pair leads the boron-containing compound to localize at the tumor sites, thereby effecting selective delivery of boron atoms to the tumor cells.

Cancer states that can be targeted and treated in accordance with the present invention include carcinomas, melanomas, sarcomas, neuroblastomas, leukemias, lymphomas, gliomas and myelomas.

A common binding pair used in pre-targeting methods is avidin or streptavidin and biotin. Avidin, found in egg whites, has a very high binding affinity for biotin, which is a B-complex vitamin. Wilcheck et al., *Anal. Biochem.*, 171: 1 (1988). Streptavidin (SAv), derived from *Streptomyces avidinii*, is similar to avidin, but has lower non-specific tissue binding, and therefore often is used in place of avidin. Both avidin and streptavidin have a tetravalency for biotin, thus permitting amplification when the former bind to biotin.

The streptavidin-biotin system represents the strongest non-covalent biological interaction known between a protein and a ligand ($K_a=10^{15}M^{-1}$). Rosebrough, *Nucl. Med. Biol.*, 20: 663–68 (1993). Accordingly, it is used in a preferred embodiment of the invention. Streptavidin is a tetramer with a molecular weight of 60 KD, with four biotin recognition sites, while biotin is a small organic molecule. Streptavidin can be covalently modified at its lysine residues and attached to an antibody. Biotin can be readily transformed at its carboxyl terminus for attachment to numerous species, including a boronated dextran. The strong streptavidin biotin interaction will lead to binding of the two components in vivo.

Streptavidin has pI of $^-6$ compared to >10 for avidin, which renders SAv's charge close to neutral at physiological pH in contrast to avidin's strong positive charge. Moreover, avidin is 'sticky' in vivo and in vitro. Rosebrough, supra. For these reasons, streptavidin is preferred to avidin for preparing conjugates used in accordance with the present invention. However, both avidin and streptavidin may be used, and, as used in the description below, the terms avidin and streptavidin include both avidin and streptavidin.

Modified forms of avidin, such s deglycosylated avidin and/or neutralized avidin, also may be used in accordance with the present invention, as may recombinant forms of avidin or streptavidin.

The present invention includes methods wherein there is a reduction of the immunogenicity of avidin or the targeting composition by coupling the immunogenic agent with a carbohydrate polymer or polyol groups. Examples of useful carbohydrates or polyol groups include dextran, polysaccharides, polyethylene glycol (PEG), and the like.

Other pre-targeting methods useful in accordance with the present invention are described, for example, in co-pending U.S. application Ser. No. 08/486,166, the contents of which are incorporated herein in their entirety. For example, the specific hybridization of complementary polynucleotide fragments, including DNA, RNA and synthetic analogs of polynucleotides such as PNAS, may be used as the recognition mechanism of a pre-targeting system. In such a method, one strand of a polynucleotide acts as one member of a binding pair, and the complementary strand acts as the complementary member of the binding pair. See also Bos et al., *Cancer Res.* 54: 3479–3486 (1994). A major advantage of this system over biotin/avidin systems could be the presumed lower immunogenicity of a relatively short piece of DNA compared to the 60,000 Dalton avidin species.

Another approach to pre-targeting involves administering an enzyme linked to an antibody, followed by administering a high-affinity enzyme inhibitor (specific for the enzyme) bound to a chelate-isotope complex. This method has the advantage over previous bispecific methods of retaining both antigen binding sites of the antibody, and the further advantage of utilizing a high affinity ($K_d$, dihyrofolate reductase:methotrexate=$10^{-10}$) secondary targeting mechanism. Enzyme and enzyme substrate combinations also may be used as binding pairs in pre-targeting methods. As with the DNA method discussed above, less antigenicity may be observed than in the avidin/biotin system.

Yet another approach to pretargeting comprises the use of a double stranded polynucleotide as one member of a binding pair, and an interclating agent as the other member of the binding pair. For example, a double stranded oligonucleotide can be attached to an antibody or antibody fragment for targeting to tumor cells. Then, a boron-containing compound comprising boron and an appropriate intercalating agent is administered, that localizes at the tumor cells by way of affinity between the oligonucleotide and intercalating agent.

While the examples set forth herein describe the use of avidin and biotin as the binding pair, any binding pair my be used in accordance with the present invention in the manner described for avidin and biotin.

Antibodies or antibody fragments may be used to pretarget the first member of the binding pair to the tumor sites.

Monoclonal antibodies are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present invention. It will be appreciated that newer techniques for production of monoclonals can also be used, e.g., human monoclonals, interspecies monoclonals, chimeric (e.g., human/mouse) monoclonals, genetically engineered antibodies and the like.

Antibody fragments useful in the present invention include F(ab')$_2$, F(ab)$_2$, Fab', Fab, Fv and the like, including hybrid fragments. Preferred fragments are Fab', F(ab')$_2$, Fab, and F(ab)$_2$. Also useful are any subfragments retaining the hypervariable, antigen-binding region of an immunoglobulin and having a size similar to or smaller than a Fab' fragment. This includes genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole immunoglobulin. The fragments may also be produced by genetic engineering.

It should be noted that mixtures of antibodies and immunoglobulin classes can be used, as can hybrid antibodies. Multispecific, including bispecific and hybrid, antibodies and antibody fragments are useful in the methods of the present invention, and are comprised of at least two different substantially monospecific antibodies or antibody fragments, wherein at least two of said antibodies or antibody fragments specifically bind to at least two different antigens produced by or associated with the cancer cells or at least two different epitopes or molecules of a marker substance produced by or associated with the cancer cells. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. No. 4,474,893 and 4,479,895, and in Milstein et al., *Immunol. Today*, 5: 299 (1984).

Preferred are antibodies having a specific immunoreactivity to a marker substance produced by or associated with the cancer cells of at least 60% and a cross-reactivity to other antigens or non-targeted substances of less than 35%.

As disclosed above, antibodies against tumor antigens are known. For example, antibodies and antibody fragments which specifically bind markers produced by or associated with tumors have been disclosed, inter alia, in Hansen et al., U.S. Pat. No. 3,927,193, and Goldenberg, U.S. Pat. Nos. 4,331,647, 4,348,376, 4,361,544, 4,468,457, 4,444,744, 4,818,709 and 4,624,846. For example, U.S. Pat. No. 4,818,709 describes monoclonal Class III anti-CEA antibodies which bind to CEA but do not bind to CEA-like antigens NCA and MA. In particular, antibodies against an antigen, e.g., a gastrointestinal, lung, breast, prostate, ovarian, testicular, brain or lymphatic tumor, a sarcoma or a melanoma, are advantageously used.

The antibodies and antibody fragments useful in the methods of the present invention may conjugated by a variety of methods known in the art. Many of these methods are disclosed in the above-referenced U.S. Patents and Patent Applications. See also Childs et al., *J. Nuc. Med.*, 26: 293 (1985).

An antibody preferred for use in the present invention is MN-14, a second generation CEA-antibody that has ten times more affinity for CEA than the first generation version, NP-4. Hansen et al., *Cancer*, 71: 3478–85 (1993). MN-14 internalizes slowly, making it suitable for a pre-targeting approach.

While antibodies are preferred targeting agents, other targeting agents also may be used, such as those described in U.S. application Ser. No. 08/486,166, the contents of which are incorporated by reference herein in their entirety.

The present invention also provides a boron-containing compound comprising a conjugate comprising biotin and boron atoms. The biotin is preferably a biotinidase-resistant biotin analog, described in more detail below. The biotin is attached to an intermediate carrier which, in turn, is coupled to approximately 1,500 boron atoms. The intermediate carrier may be, for example, dextran. Other carrier molecules will be apparent to those skilled in the art and include aminodextrans, Shih et al., U.S. Pat. No. 5,057,313, other polysaccharides, natural and synthetic polypeptides, such as polylysines, polyglutamic acids and polycysteines, and synthetic polymers, such as polyethyleneimine, polyolefins, polyalcohols, polycarboxylic acids and starburst dendrimers. Another example of suitable carriers are copolymers, such as those with the formula $(Lys)_n$-$(aax)_q$-$(Glu)_m$-$(aay)_p$, where n, m, p and q are integers and aax and aay are non-specified amino acids which may be the same as or different from each other, and which are selected from the natural amino acids and their D-isomers.

In one embodiment, there are from about 1 to about 3 biotin moieties conjugated to each dextran molecule. In order to achieve optimal delivery of boron-10 atoms to tumor sites, it is desired to have an average of just one biotin moiety per each molecule of the biotin-dextran-boron compound. Because each molecule of avidin or streptavidin can bind up to four molecules of biotin, up to 6000 atoms of boron can be delivered per mole of antibody pre-localized at the tumor sites. Ideally, each of the streptavidin's four biotin-binding sites will be loaded with a biotin-dextran-$(boron)_x$ moiety.

The boron-containing compound of the present invention amplifies the amount of boron that can be delivered per antibody molecule used in the first pre-targeting step, and is an important advantage of the present invention. The use of this compound in accordance with the present invention achieves or surpasses the high boron concentration in tumor required for effective BNCT. Accordingly, the compositions and methods of the present invention are useful for targeting boron atoms to tumor sites for therapy of common malignant tumors by BNCT.

While the boron-containing compound is described above as a biotinylated compound, the present invention includes embodiments where the boron-containing compound comprises a conjugate comprising boron atoms and any member of a binding pair, such as a polynucleotide, enzyme or enzyme substrate, as discussed above.

In a preferred embodiment, the boron-containing compound also is radiolabeled with a detectable label. This permits the determination of the location of the administered boron-containing compound. Suitable radiolabels are known to those skilled in the art, and include, for example, gamma-emitting isotopes. The compound may be labelled by methods known in the art. For example, the boron-containing compound may be conjugated to a chelating agent such as, for example, DTPA, which chelates the radiolabel, or a thiol ligand for direct labeling by Tc-99m using known methods, such as those described in U.S. Pat. No. 5,514,363. When a radiolabeled boron-containing compound is used, the radiolabel can be detected before the boron is irradiated to ensure that the compound has localized at the tumor cells and that non-localized boron has cleared from circulation. This embodiment minimizes the risks of damaging healthy cells when the boron is irradiated, because irradiation can be delayed until the boron-containing compound has localized at tumor cells. The neutron beam advantageously is focused to sites of localized boron-10 moieties to further improve the precision of neutron capture.

In a preferred embodiment of the present invention, the sulfhydryl-containing boron moieties, sodium borocaptate or BSH ($Na_2B_{12}H_{11}SH$), are used for boronating dextran. These have been documented to be non-toxic. Barth, *Cancer Res.*, supra; Haselberger et al., *Cancer Res.* 54: 6318–20 (1994). These are preferably boron-10 enriched, containing, for example up to 95–98% boron-10.

Preparation of a borocaptate-dextran conjugate is illustrated in Scheme I below. Other boron-10 enriched compounds also are known, such as boron-10-enriched carboranes. Examples of these are described in U.S. Pat. No. 4,824,659, the contents of which are incorporated herein by reference in their entirety. These compounds may be used in accordance with the present invention, for example, by conjugating the carboranes to the chosen carrier.

In one embodiment of the present invention, a two-step pre-targeting approach is used. As with the other embodiments of the invention, this approach separates the antibody localization step from the step of depositing boron at the tumor sites. For example, tumor sites are pre-targeted with an avidin or streptavidin-MAb conjugate. After a time period for tumor targeting has passed, a non-antibody, biotinylated boron-containing compound, such as the boron-containing compounds described above, is administered. This compound binds to the avidin or streptavidin localized at the tumor sites via the biotin moiety, thereby delivering boron atoms to the tumor sites. This method avoids concerns about the in vivo behavior of boronated antibodies because the boron-containing compound does not comprise an antibody.

Binding pairs other than biotin and avidin may be used, such as the polynucleotides and enzyme/enzyme substrate pairs discussed above.

After the biotinylated boron compound has localized at the tumor site, the boron atoms may be irradiated according to conventional BNCT methods, thereby effecting therapy of the tumor cells.

Another embodiment of the present invention uses an intermediate step between the antibody conjugate delivery step and the boron delivery step. In this step, a clearing agent is used to effect the rapid clearance of circulating antibody and ensure that the final boron concentration in circulation is kept negligible or non-existent.

In one embodiment, the clearing agent comprises a conjugate comprising galactose, human serum albumin (HSA) and biotin. Such a clearing agent is cleared quickly from circulation by asialoglycoprotein receptors in the liver.

In another preferred embodiment, the clearing agent is an anti-idiotypic antibody, as described in U.S. application Ser. No. 08/486,166. This antibody may be galactosylated to achieve rapid clearance as described above.

Routes of administration of the compositions used in the present invention include intravenous, intraarterial, intrapleural, intraperitoneal, intrathecal, subcutaneous or by perfusion.

The timings of the two or three pre-targeting steps can be optimized to enhance the efficiency of boron delivery. The time of maximum tumor uptake of the antibody conjugate, for example, of streptavidin-MN14, can be determined by first determining the optimum SAv dose, and also determining the time of maximum tumor uptake at this dose. In one test, the time of maximum tumor accretion was found to be between 48 hours and 72 hours Optimally, the clearing agent, such as unlabeled glycosylated HSA-biotin or anti-idiotypic antibody, is administered at this time.

In different pre-targeting methods, the clearing agent was administered 24 hours after the injection of a streptavidin-IgG conjugate. Axworthy et al., WO 93/25240. This "early" timing may avoid the substitution of some streptavidin sites by endogenous biotin. Hnatowich et al., *Nucl. Med. Commun.* 15: 575–77 (1994).

A clearing agent comprising a galactose-HSA-biotin conjugate drops the level of circulating primary mAb-SAv conjugate down to about 5% ID/g. From initial studies, the present inventors have shown that the blood level of the antibody conjugate drops dramatically at the 'zero' time upon administering an anti-idiotypic clearing agent. That is, circulating conjugate is cleared virtually instantaneously. The biotinylated boron-containing compound, therefore, may be administered within hours (2–4 h) of the clearance step, and may be administered immediately after the clearance step when an anti-idiotypic clearing agent is used.

The attainment of low levels of circulating boron, and, in particular, the attainment of near absolute clearance of circulating boron, has the advantage of reducing the systemic toxicity observed when boron atoms are irradiated by the neutron beam. That is, because little or no boron is in circulation, only targeted tumor cells are affected by the irradiation of boron atoms by the neutron beam.

In one embodiment of the invention, an anti-idiotypic clearing agent is used, the boron-containing compound is administered, and the patient is exposed to a thermal neutron beam shortly after the boron-containing compound is administered, for example, immediately after the boron-containing compound is administered, thereby irradiating the boron atoms at time when the amount of boron localized at the targeted tumor cells is at a maximum. In a variation of this embodiment, the boron-containing compound is labeled with a detectable label, and the detectable label is detected prior to the irradiation of the boron atoms. This latter variation allows the practitioner to ensure that the boron-containing compound is localized before the boron is irradiated, thereby minimizing the risks of damage to healthy cells.

Alternatively, the boron-containing compound can be administered parenterally within 24 hrs of the 2nd step, or up to 3 days later. The longer the delay after the first step, the lower the amount (and ratio) of clearing agent needed.

In one embodiment of the invention, no clearing agent is used, and the boron-containing compound is administered from about 5 to about 20 days after the administration of the antibody conjugate. This embodiment is advantageous for patients who show rapid blood clearance and tumor accretion of the targeted compounds, for example, because they have a heavy tumor burden which is expressing large amounts of antigen.

The optimum dosage of the biotinylated boron compound to administer is a function of the amount of avidin or streptavidin which must be complexed by the compound, as well as a function of the compound's in vivo clearance kinetics. As discussed below, biodistributions of I-125-labeled biotin-dextran-(boron)$_x$ in balb/C normal mice at five time-points yield this information. The double labeling experiment in tumor-bearing nude mice (3rd step) delineates incorporation of boronated material in tumor and other organs. Depending on how long it takes for the I-125 label to clear from non-target organs, the timing and dosage of the third-step can be modified.

In an embodiment of the method of the present invention, antibody-binding pair member conjugate, such as an antibody-avidin or antibody-polynucleotide conjugate, is injected parenterally, usually at an antibody dose of up to 1 g, for example within a dose range of from about 50 mg to about 500 mg. This can be administered as a single injection or in divided doses.

After 1–5 days, more preferably at less than 2 days and even at less than 1 day when the first agent involves a small and rapidly targeting molecule, such as an antibody fragment or subfragment, a dose of unlabeled clearing agent may be administered parenterally. The dose may be, for example, 2.5 to 10 times the dose of the first step (which can be determined also by measuring the amount of antibody from the first step circulating in the blood at the time of the second step's injection). The clearing agent can be given as a single injection or in divided doses, wherein administering the clearing agent in 2 doses is preferred in certain circumstances.

Then, the binding pair member-boron compound, such as a biotinylated boron compound, is administered at the appropriate time and dosage, determined as described above. For example, when the avidin-biotin system is used as the binding pair, the dose of biotinylated boron may be from about 2 mg to about 2 g. The higher dose represents approximately a 4× molar excess of biotinylated compound to the injected avidin-antibody conjugate, which permits saturation of all biotin-binding sites on the pre-targeted avidin conjugate. The lower dose reflects the observation that only a small amount of the biotinylated boron compound needs to reach the tumor sites.

The embodiments of the invention may be further illustrated through examples which show aspects of the invention in detail. These examples illustrate specific elements of the invention and are not to be construed as limiting the scope thereof.

I. PREPARATION OF REAGENTS

Preparation and analysis of streptavidin-MN-14 Ab conjugate:

A thiolated MN-14-IgG is reacted with a maleimido-appended streptavidin. A typical optimized conjugation involves using a 5-fold molar excess of commercially available sulfo-SMCC linker (sulfosuccinimidyl 4-[N-maleimidomethyl] cyclohexane-1-carboxylate) for streptavidin derivatization, a 5-fold molar excess of 2-iminothiolane for thiolating MN-14, and about a 1:1 molar ratio of proteins, at pH 6.4, for coupling. Preparative HPLC purifications on a Spherogel TSK-G 3000-SWG column (Tosohaas, Montgomeryville, Pa.), using 0.2M phosphate buffered saline at pH 6.8 separates the 1:1 conjugate from unreacted starting materials and aggregate.

Analysis of the streptavidin-IgG conjugate on SDS-PAGE indicated a molecular weight of about 210K daltons. Biotin binding assays carried out using an In-111-labeled biotin-(ITC-Bz-DTPA) derivative revealed an uptake of four equivalents of biotin-DTPA by one equivalent of streptavidin-IgG conjugate, thus establishing both conjugate purity and the preservation of all of the four biotin binding domains in the conjugate.

In vitro competitive binding studies using ELISA assays have shown that the binding affinity for the antigen (CEA) was very similar to that of unmodified MN-14.

In vivo targeting experiments in GW39 tumored nude mice using I-125 labeled SAv-MN14-IgG and I-125 labeled unmodified MN-14-IgG showed similar targeting and clearance patterns as shown in Table 1 below.

TABLE 1

Biodistributions of I-131-MN14(A) and I-125-[SAv-MN14] (B) in GW39 tumor bearing nude mice (% ID/g,n = 5)

| Tissue | | 24 h | 72 h | 168 h |
|---|---|---|---|---|
| GW39 Tumor: | A | 15.37 ± 6.34 | 19.71 ± 6.22 | 95.77 ± 46.4 |
| | B | 12.18 ± 4.74 | 12.52 ± 3.19 | 57.91 ± 29.0 |
| Liver: | A | 3.79 ± 0.70 | 2.74 ± 0.41 | 1.46 ± 0.36 |
| | B | 4.49 ± 0.30 | 3.78 ± 0.53 | 1.80 ± 0.26 |
| Spleen: | A | 3.20 ± 0.89 | 2.67 ± 0.46 | 1.25 ± 0.43 |
| | B | 2.31 ± 0.62 | 2.86 ± 0.48 | 1.68 ± 0.21 |
| L. Kidney | A | 4.93 ± 1.14 | 2.56 ± 0.42 | 1.39 ± 0.54 |
| | B | 3.43 ± 1.34 | 1.78 ± 0.20 | 1.31 ± 0.16 |
| Lungs: | A | 7.34 ± 0.43 | 4.10 ± 0.92 | 2.64 ± 0.83 |
| | B | 5.34 ± 0.71 | 2.15 ± 0.19 | 1.43 ± 0.04 |
| Blood: | A | 14.00 ± 0.81 | 9.97 ± 1.44 | 5.22 ± 1.51 |
| | B | 11.39 ± 0.88 | 7.56 ± 0.88 | 2.82 ± 0.82 |

The MN14-streptavidin conjugate made and purified by the above-described method is a preferred conjugate for use in the first pre-targeting step of the present invention.

Preparation of Galactosyl-HSA-biotin clearing agent:

HSA is biotinylated using commercially available sulfo-succinimido biotin in phosphate buffer at pH 7.5–8.0. Cyanomethyl 2,3,4,6-tetra-O-acetyl-1-thio-β-D-galactopyranoside is reacted with 10% v/v 0.1M sodium methoxide in methanol to generate the amine-reactive galactosyl thioimidate derivative. Stowell et al., *Adv. Carbohydr. Chem. Biochem.*, 37: 225–81 (1980). The biotinylated HSA, buffered at pH 7.5–9.0, is incubated with various molar excess amounts of the thioimidate, and the glycosylated antibody is purified by size-exclusion chromatography.

The extent of glycosylation is gauged indirectly by determining the available amino groups on HSA before and after glycosylation. This involves reaction with fluorescamine, and determination of the fluorescence intensity in a fluorometer. Stocks et al., *Analyt. Biochem.*, 154: 232–34 (1984).

The levels of biotinylation and galactosylation of human serum albumin needed to complex circulating SAv-MN14 without complexing tumor-localized conjugate, and to quickly clear from circulation can be optimized by preparing different conjugates differing in the galactose and biotin substitution ratios, and comparing the clearance.

This galactose-HSA conjugate is useful as a clearing agent in the methods of the present invention.

Preparation of a biotin-dextran-boron compound:

1. Preparation of a sulfhydrylborane-dextran conjugate (compound 3 in Scheme I):

70,000 MW dextran is boronated with borocaptate using a published 2-step procedure. Holmberg et al., *Bioconjugate Chem.*, 4: 570–73 (1993). This simple method involves allylation of the dextran's hydroxyl groups, followed by a free-radical type addition of borocaptate. This method has been found to incorporate 100–125 boron cages, or 1200–1500 boron atoms, per dextran chain. The product obtained by this method is water soluble. According to Holmberg et al., supra, 70% of the hydroxyls were allylated and a 50% efficiency in the boronation of allyl dextran resulted in the conjugate having boron content of 150 $\mu$g boron/mg and a sulfur content of 1.5–4%. This corresponds to 100–120 boron cages, or 1200–1500 boron atoms, per dextran chain.

In particular, dextran (2 g, 70 kD) was allylated in aqueous solution with 29 mmol of allyl bromide in the presence of 12.5 mmol of sodium hydroxide for 2 h at 60° C. After this time the reaction mixture was acidified, repeatedly precipitated from acetone, washed several times with ethanol and finally dialyzed. The intermediate product was then made basic with 40 mmol of sodium hydroxide and reacted with 2.8 g of 6-bromohexanoic acid at 70°–80° C. for 5 h. The solution was cooled, acidified and purified by dialysis.

The doubly derivatized dextran is boronated by reaction of dextran allyl groups with sodium borocaptate ('BSH' or $Na_2B_{12}H_{11}SH$; di-sodium undecahydro-mercapto-closo-dodecacarborate; Boron Biologicals, Raleigh, N.C.). Briefly, allyl dextran (20 mg) was reacted with 30 mg of sodium borocaptate and 20 mg of ammonium persulfate in 2 mL of water for 3 h at 50° C. The intermediate product is purified by PD-10 column chromatography and by repeated dialysis against water.

Boron content of the sulfhydrylborane-dextran conjugate is determined using ICP-atomic emission spectroscopy, as well as from sulfur content. Sulfur analysis indicated the presence of 124.3 boron cages while microanalysis for boron content gives a figure of 137 boron cages (1644 boron atoms) per mole of dextran. Boron determinations of non-biological samples can be carried out by commercial outlets (Galbraith Laboratories).

The carboxylic acid derivatized boronated dextran-70 (12.5 mg) was treated with 1-ethyl-3-(3-dimethylamino-propyl) carbodiimide (12.5 mg) and a fifty-fold excess of ethylene diamine at pH 5.3 for 4 h at room temperature. Excess reactants were removed from the polymeric intermediate by repeated filtration through a Centricon-30 membrane and the purified intermediate was buffer-exchanged into 0.1M phosphate buffer at pH 7.7. This material was reacted with a fifteen-fold molar excess of sulfosuccinimido biotin for one hour and finally purified using a Centricon-30 membrane. HABA assay indicated that the biotinylated-boronated-dextran-70 contained approximately two biotin moieties per polymeric unit.

While 70 KD molecular weight dextran is used in this example, in vivo pharmacokinetics of the boronated dextran may make the use of either higher or lower molecular weight dextran preferable.

2. Carboxyalkylation of sulfhydrylborane-dextran conjugate:

To react with an amine-containing biotin analog, the dextran conjugate is first derivatized with 6-bromohexanoic acid to introduce the necessary carboxylic acid groups. Carboxyalkylation and the allylation reaction described above are both chemically the same type of alkylation reaction. These two reactions can be combined in one operation by first reacting dextran, under basic conditions, with allyl bromide, and then reacting with bromohexanoic acid. A similar tandem operation has been described for the conjugation of mitomycin with an antibody using dextran as intermediate carrier. Noguchi et al., *Bioconj. Chem.*, 3: 132–37 (1992).

The order of alkylation is designed to limit the level of carboxylic acid groups introduced so as to achieve a biotin-dextran ratio of about one in the next step. The extent of carboxyalkylation is determined by titration with sodium methoxide. Any slight reduction in the number of boron atoms introduced as a result of this "double derivatization" should not be too worrisome due to the large number of boron atoms loadable by this method, and due to the 4-fold amplification of boron localization per mole of the SAv-IgG conjugate localized at tumor sites.

3. Biotinylation of sulfhydrylborane-dextran (Scheme 1):

A preferred embodiment of the present invention uses a specially designed amine-containing biotin analog (compound 7 of Scheme 1). This compound has a spacer arm between the biotin moiety and the amine terminus, and has a N-methyl substitution at the biotin peptide bond. Alternatively, a biotinidase-resistant biotin analog comprising a biotin peptide-bonded to an unnatural D-amino acid, and further terminating in an amino group for conjugation to carboxyl-substituted dextran borocaptate, may be used. These characteristics of the specific biotin-peptide bond prevent or minimize recognition by serum biotinidases, and the compounds are therefore more stable. Evangelatos et al., *Analyt. Biochem.*, 196: 385–89 (1991).

The amine-containing biotinylation agent is condensed with carboxyalkylated sulfhydrylborane-dextran using water soluble carbodiimide ('EDC') and N-hydroxy sulfo-succinimide at a pH of about 6 at room temperature. The structure of the requisite final product is shown as compound 4 in Scheme 1.

The extent of amide formation may be controlled by varying the molar excess of amine used. Noguchi et al., supra. Such manipulation can be used to control the amount of biotin introduced, with the goal of introducing an average of about 1 biotin moiety per dextran chain. Final molar substitution ratios are derived from determinations of biotin-dextran and boron-dextran ratios, and from binding to known concentrations of streptavidin.

II. ANIMAL EXPERIMENTS

LS174T cell tumor xenograft nude mouse model is used for animal experiments. Tom et al., In-Vitro, 12: 180–91 (1976). Tumor cells are grown in cell culture prior to sub-cutaneous or intramuscular injection of $5 \times 10^6$ cells into nude mice. Tumors take from 10–14 days to grow to a useful size (50–100 mg), at which time animals are ready for use.

10 $\mu$Ci/mouse of radioiodinated antibody conjugate or biotinylated sulfhydryl-borane are used. Groups of five mice are used to determine biodistributions at each time-point in pharmacokinetic studies involving the first two steps of pre-targeting, the administration of the streptavidin-MAb conjugate and the clearing step.

For biodistributions using animals successively used in all of the three steps, including the third step of boron delivery, up to ten mice per time-point are examined. of these, some (3 to 5) are used exclusively for the determination of boron biodistributions. These coded mice will be given only cold SAv-MN14 and biotin-dextran-(boron)$_x$, although with identical protein and dextran doses, but otherwise subjected to identical experimental conditions as nude mice which will be examined with radioiodinated compounds.

The protein dose of the first step reagent (I-131-MN14-SAv) needed to saturate tumor cells and the time of maximum tumor accretion at that dose of the conjugate is determined by administering 10, 50, 100 and 250 $\mu$g of the conjugate (using additional unlabeled conjugate as needed)

to four groups of tumored mice, and determining biodistributions at 1, 2, 3, and 5 days for each group of five mice.

Immunoreactivity of I-131-labeled SAv-MN14 is assessed by complexing with an 80-fold excess of antigen CEA (Scripps Clinic, La Jolla, Calif.), and analyzing the shift of HPLC retention to near void volume of the column. Routine in vitro competitive binding assays also may be performed with the SAv-MN14 preparations.

The clearance of circulating SAv-MN14 conjugate is assessed using the biotin-HSA-galactose conjugate described above. This is done by administering I-125-labeled second MAb to 3 groups of mice (5/group) already carrying I-131-SAv/MN14 at the time of maximal tumor uptake. Biodistributions of both the labels are determined at 2, 4, and 24 hours post-injection of the second MAb.

Tom et al., In-vitro, supra, describes a method for radioiodinations with I-131 and I-125 isotopes using a chloramine T procedure. A typical radioiodination is as follows: 0.5M sodium phosphate pH 7.4 (50 μl), antibody (51 μg/0.85 mCi of iodide), and chloramine T (4.25 μg) are added to the vial containing radioactive iodide. After about 1 hour, sodium metabisulfite (8.5 μg in 50 μl water) is added, and the labeled product is purified by passing through a PD-10 column (Pharmacia). Recovery of radioactivity is about 70%. This procedure may not be preferred for the radioiodination of streptavidin-mab conjugates, however, due to the oxidative instability of streptavidin because of tryptophan residues in its biotin-binding domain.

The following method is preferred: [I-125]-N-succinimidyl-4-iodobenzoate (1.7 mCi, NEN DuPont) is dried in a stream of air for 40 minutes to remove the organic solvent and treated with 200 μg of streptavidin-mab in 500 μL of 0.5M borate buffer at pH 9.5. The reaction is allowed to proceed for 1 h at room temperature, at which time the reaction is quenched by the addition of 1M glycine at pH 8.5, and the reaction mixture is allowed to stand for a further hour. The radioiodinated SA-mab product is purified on a PD-10 column equilibrated in 1% HSA in PBS at pH 7.0. An radiochemical yield of approximately 55% is obtained.

Similar determinations are performed to assess clearance with other cleaning agents, such as an anti-idiotype antibody.

For animal experiments involving the third step, the boron delivery step, the second stage clearing agent is not radiolabeled. Instead, the clearance pattern of the first antibody is monitored using its own label. For the analysis of the third step, the fate of I-125 label attached to antibody and I-131, now attached to boron cages, is ascertained in in vivo pharmacokinetic experiments.

A number of examples exist for the iodination of boronated compounds using different methods. Varadarajan et al., *Bioconj Chem*, 2: 102–110 (1991). The material is purified on PD-10 disposable column, and the purity is assessed on a analytical Biosep-SEC-S4000 (Phenomenex, Torrance, Calif.) size-exclusion column which is suitable for analysis of dextrans (water as mobile phase). Radioactive as well as refractive index detection are employed. If the purity is assessed to be less than 90%, elimination of possible smaller radioiodine impurities is achieved by Centricon 30 microconcentrator (Amicon, Danvers, Mass.).

Quantitative boron determinations are carried out to characterize the biotinylated dextran-boron compound, and to determine boron accumulation in vivo in tumor at different times post-administration of the boron compound in animal experiments. Boron determination is conducted on animal tissue using the prompt-γ method which is sensitive in determining sub-ppm levels of boron. Fairchild et al., *Cancer Res*, 50: 4860–4865 (1990).

Efficiency of a Three-Step Pre-Targeting Method:

The SAv-MN14 conjugate described above was used for in vivo biodistribution determinations in nude mice bearing human colon carcinoma xenografts. The second step involving clearance of circulating conjugate was accomplished by using either a galactosylated anti-idiotypic second antibody, or a galactose-HSA-biotin complex. For the third step, an In-111-labeled biotin compound comprising the biotinidase-resistant structural feature described above was used. Excellent tumor-to-non-tumor ratios were obtained for In-111 biodistributions, as seen in Table 2. Table 2 reflects the fact that almost all of the conjugate has been cleared from circulation by using the second step clearing agent.

TABLE 2

Biodistributions of In-111-labeled biotin compound in GW39 bearing nude mice (% ID/g, n = 3) after pre-targeting with SAv-MN14, clearance of circulating conjugate with a galactose-HSA-biotin cleaning agent, and the administration of the third step biotin compound. The clearance of the first step agent from circulation is evidenced by non-complexable conjugate in blood. Low levels in normal organs reflect the absence of biotin-recognizing sites of the conjugate.

| Tissue | 4 h | 24 h | 96 h |
| --- | --- | --- | --- |
| GW39 Tumor | 3.13 ± 2.84 | 8.40 ± 5.33 | 6.30 ± 1.51 |
| Liver | 0.22 ± 0.07 | 0.33 ± 0.01 | 0.21 ± 0.11 |
| Spleen | 0.20 ± 0.08 | 0.19 ± 0.06 | 0.33 ± 0.14 |
| L. Kidney | 1.61 ± 0.80 | 0.93 ± 0.21 | 0.85 ± 0.18 |
| Lungs | 0.30 ± 0.11 | 0.20 ± 0.12 | 0.08 ± 0.03 |
| Blood | 0.60 ± 0.24 | 0.37 ± 0.32 | 0.05 ± 0.03 |

A third-step compound incorporating a dextran-borocaptate moiety as described above achieves similar tumor:non-tumor ratios as those exhibited by this non-boronated compound.

III. METHODS FOR TARGETING BORON ATOMS TO TUMOR CELLS

The following example illustrates a two-step pre-targeting method in accordance with the present invention. The two steps are as follows:

Step 1: The SAv-MN14 conjugate described above is administered to a cancer patient, and allowed to localize at tumor sites.

Step 2: The biotinylated dextran-borocaptate compound describe above is administered, and localizes at the tumor sites due to the affinity between the biotin moieties on the compound and the streptavidin moieties localized at the tumor site in step 1.

Once the boron has localized at the tumor site, it may be irradiated in accordance with conventional BNCT methods to effect therapy of the tumor cells.

The following example illustrates a three-step pre-targeting method in accordance with the present invention. The three steps are as follows:

Step 1: The SAv-MN14 conjugate described above is administered to a cancer patient, and allowed to localize at tumor sites.

Step 2: Circulating conjugate is cleared using the galactose-HSA-biotin compound described above. Biotin-SAv complexation will result in a fast clearance of the galactose-appended complex (gal-HSA-biotin-SAv-MN14), from circulation, by asialoglycoprotein receptors in liver. Ong et al., *Cancer Res.*, 51: 619–26 (1991).

Alternatively, a galactosylated anti-idiotypic antibody may be used as the clearing agent.

Step 3: The biotinylated dextran-borocaptate compound described above is administered, and localizes at the tumor sites due to the affinity between the biotin moieties on the compound and the streptavidin moieties localized at the tumor site in step 1.

Once the boron has localized at the tumor site, it may be irradiated in accordance with conventional BNCT methods.

The following example illustrates a preferred method in accordance with the present invention. The method comprises:

1. Administering the SAv-MN14 conjugate described above to a cancer patient, and allowing the conjugate to localize at tumor sites.

2. Administering a clearing agent, such as the galactose-HSA-biotin complex described above or an anti-idiotypic antibody, to clear non-localized conjugate from circulation.

3. Administering a biotinylated dextran-borocaptate compound that is labelled with a detectable label, and allowing this compound to localize at the tumor sites due to the affinity between the biotin moieties on the compound and the streptavidin moieties localized at the tumor site in the first step.

4. Detecting the detectable label on the biotinylated dextran-borocaptate compound to ensure that the boron-containing compound has localized at tumor cells and that non-localized boron-containing compound is cleared from circulation.

5. Irradiating the boron atoms localized at the tumor site, thereby effecting BNCT of the tumor cells.

It will be apparent to those skilled in the art that various modifications and variations can be made to the processes and compositions of this invention. Thus, it is intended that the present invention cover the modifications and variations of this invention provided they come within the scope of the appended claims and their equivalents.

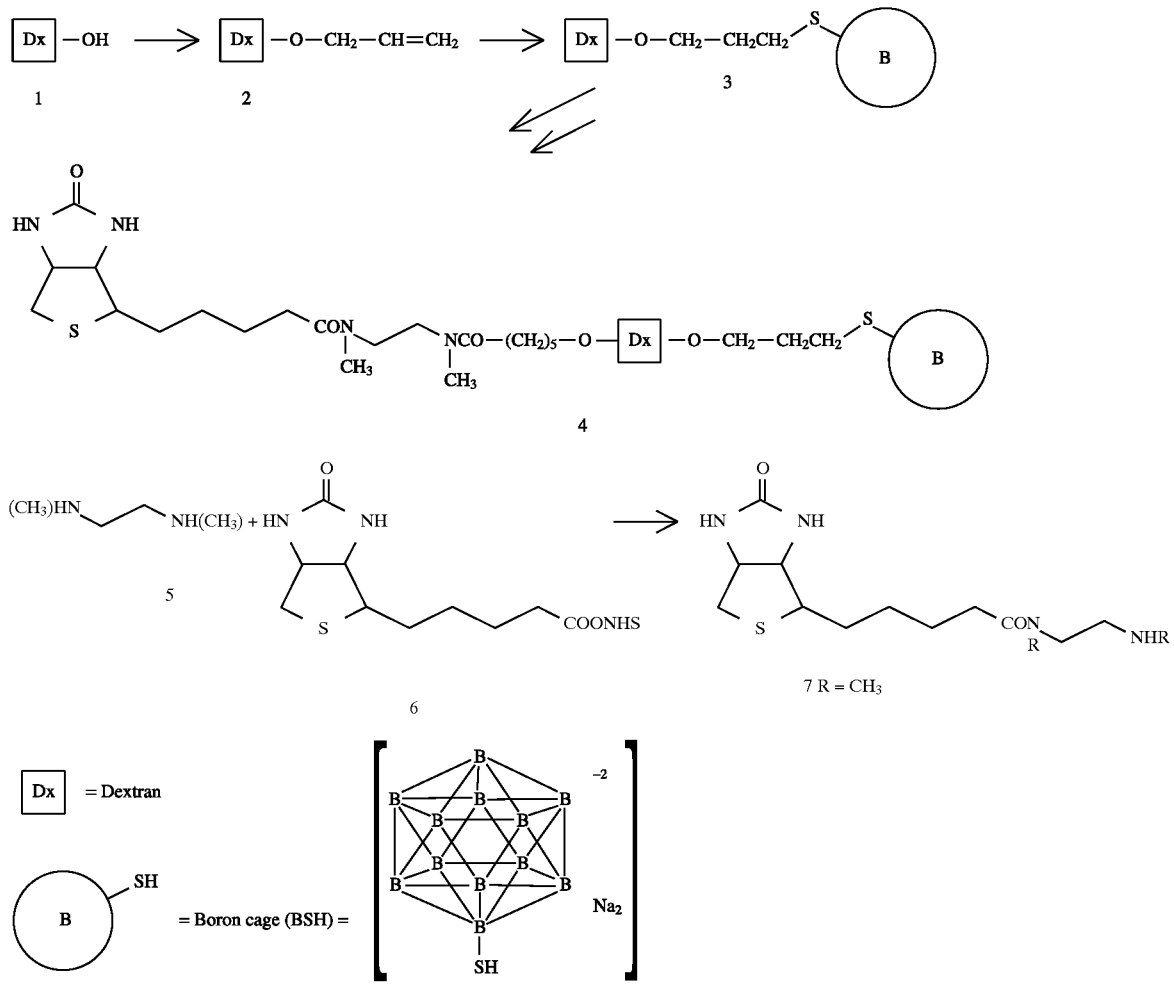

What is claimed is:

1. A method for targeting boron atoms to tumor cells in a patient comprising:

(A) administering to said patient a targeting composition comprising a conjugate of a first member of a specific binding pair and an antibody or antigen-binding antibody fragment, wherein said antibody or antibody fragment selectively binds to a characteristic intracellular or cell surface antigen produced by or associated with said tumor cells and present at said tumor cells, and allowing said targeting composition to localize at said tumor cells;

(B) optionally, administering to said patient a clearing composition, and allowing said clearing composition to clear non-localized targeting composition from circulation;

(C) administering to said patient a boron compound comprising a conjugate comprising a complementary member of said binding pair and boron atoms, and allowing said boron compound to localize at said tumor cells.

2. The method of claim 1, wherein said first member of said binding pair comprises streptavidin and said complementary member of said binding pair comprises biotin.

3. The method of claim 2, wherein said boron compound comprises said biotin conjugated to dextran derivatized with from about 1200 to about 1500 boron atoms.

4. The method of claim 3, wherein said dextran is derivatized with sodium borocaptate ($Na_2B_{12}H_{11}SH$).

5. The method of claim 2, wherein said biotin is provided as a biotinidase-resistant biotin analog comprising a biotin moiety bonded to an unnatural D-amino acid via a peptide bond.

6. The method of claim 2, wherein said boron compound comprises about 1–3 biotin moieties per molecule of compound.

7. The method of claim 1, wherein said first member of said binding pair is a single-stranded oligonucleotide and said complementary member of said binding pair is a complementary single-stranded oligonucleotide.

8. The method of claim 1, wherein said first member of said binding pair is an enzyme and said complementary member of said binding pair is a substrate for said enzyme.

9. The method of claim 1, wherein said first member of said binding pair is an enzyme substrate and said complementary member of said binding pair is a corresponding enzyme for said substrate.

10. The method of claim 1, wherein said first member of said binding pair is a double-stranded oligonucleotide, and said complementary member of said binding pair is an intercalating agent.

11. The method of claim 1, wherein said antibody or antibody fragment is a monoclonal antibody or antigen-binding fragment thereof.

12. The method of claim 11, wherein said monoclonal antibody is a Class III anti-CEA antibody.

13. The method of claim 1, wherein said optional clearing composition of step (B) is administered.

14. The method of claim 13, wherein said clearing composition comprises a galactosylated conjugate of human serum albumin (HSA) and biotin.

15. The method of claim 13, wherein said clearing composition comprises an anti-idiotypic antibody.

16. The method of claim 15, wherein said anti-idiotypic antibody is galactosylated.

17. The method of claim 13, wherein said boron compound of step (C) is administered within about 2 to about 24 hours after said clearing agent of step (B) is administered.

18. The method of claim 1, wherein said boron compound is radiolabeled with a detectable radioisotope.

19. The method of claim 18, further comprising the step of detecting said detectable radioisotope of said boron compound, thereby determining the location of said boron compound.

20. The method of claim 1, wherein said boron compound is administered within about 48 to about 240 hours after said targeting composition of step (A) is administered.

21. The method of claim 1, wherein said clearing composition of step (B) is not administered, and wherein said boron compound of step (C) is administered within about 5 to about 20 days after said targeting composition of step (A) is administered.

22. The method of claim 1, wherein about 6000 boron atoms per molecule of said antibody administered are localized at said tumor cells.

23. A method for effecting boron neutron capture therapy (BCNT) of tumor cells in a patient, comprising the steps of:
(A) administering to said patient a targeting composition comprising a conjugate of a first member of a specific binding pair and an antibody or antigen-binding antibody fragment, wherein said antibody or antibody fragment selectively binds to a characteristic intracellular or cell surface antigen produced by or associated with said tumor cells and present at said tumor cells, and allowing said targeting composition to localize at said tumor cells;
(B) optionally, administering to said patient a clearing composition, and allowing said clearing composition to clear non-localized targeting composition from circulation;
(C) administering to said patient a boron compound comprising a conjugate comprising a complementary member of said binding pair and boron atoms, and allowing said boron compound to localize at said tumor cells; and
(D) irradiating the boron atoms of said boron compound localized at said tumor cells, thereby effecting BNCT of said tumor cells.

24. The method of claim 23, wherein said boron compound is radiolabeled with a detectable radioisotope, and wherein said method further comprises the step of detecting said detectable radioisotope of said boron compound before said boron atoms are irradiated, thereby determining the location of said boron compound.

25. A sterile, injectable composition for human use comprising a composition for use in targeting boron atoms to tumor cells, comprising a boron compound comprising a conjugate of (i) a member of a specific binding pair selected from the group consisting of a single-stranded oligonucleotide, a double-stranded oligonucleotide, an enzyme, an enzyme substrate, and biotin, wherein said biotin is provided as a biotinidase-resistant biotin analog comprising a biotin moiety bonded to an unnatural D-amino acid via a neptide bond, and (ii) boron atoms.

26. The composition of claim 25, wherein said member of said binding pair is biotin.

27. The composition of claim 26, comprising a conjugate of said biotin and dextran derivatized with from about 1200 to about 1500 boron atoms.

28. The composition of claim 27, wherein said dextran is derivatized with sodium borocaptate ($Na_2B_{12}H_{11}SH$).

29. The composition of claim 25, wherein said boron compound is radiolabeled with a detectable label.

30. A kit suitable for use in a method for targeting boron atoms to tumor cells in a patient, the kit comprising in separate containers:
(A) a sterile, injectable preparation of a targeting composition comprising (i) first member of a specific binding pair selected from the group consisting of a single-stranded oligonucleotide, a double-stranded oligonucleotide, an enzyme, an enzyme substrate, biotin, and avidin, wherein said biotin is provided as a biotinidase-resistant biotin analog comprising a biotin moiety bonded to an unnatural D-amino acid via a peptide bond, and (ii) an antibody or antigen-binding antibody fragment, wherein said antibody or antibody fragment selectively binds to a characteristic intracellular or cell surface antigen produced by or associated with said tumor cells and present at said tumor cells;
(B) optionally, a clearing composition; and (C) a boron (i) a complementary member of said binding pair selected from the group consisting of a complementary single-stranded oligonucleotide, a complementary double-stranded oligonucleotide, an enzyme substrate for said enzyme, an enzyme for said enzyme substrate, avidin, and biotin, respectively, wherein said biotin is provided as a biotinidase-resistant biotin analog comprising a biotin moiety bonded to an unnatural D-amino acid via a peptide bond, and (ii) one or more addends comprising a plurality of boron atoms.

31. The kit of claim 30, comprising said clearing composition.

32. The kit of claim 31, wherein said clearing composition comprises an anti-idiotypic antibody.

33. A kit suitable for use in a method for targeting boron atoms to tumor cells in a patient, the kit comprising, in separate containers:

(A) a sterile, injectable preparation of a targeting composition comprising (i) a first member of a specific binding pair and (ii) an antibody or antigen-binding antibody fragment, wherein said antibody or antibody fragment selectively binds to an antigen produced by or associated with said tumor cells and present at said tumor cells;

(B) a clearing composition; and (C) a boron compound comprising a conjugate comprising (i) a complementary member of said binding pair and (ii) one or more addends comprising a plurality of boron atoms.

34. The kit of claim 33, wherein said clearing composition comprises an anti-idiotypic antibody.

* * * * *